(12) United States Patent
Grewe et al.

(10) Patent No.: US 8,303,648 B2
(45) Date of Patent: Nov. 6, 2012

(54) ARTIFICIAL VENOUS VALVE CONTAINING THERAPEUTIC AGENT

(75) Inventors: David D. Grewe, West Lafayette, IN (US); James D. Purdy, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 901 days.

(21) Appl. No.: 11/789,413

(22) Filed: Apr. 24, 2007

(65) Prior Publication Data
US 2007/0265699 A1 Nov. 15, 2007

Related U.S. Application Data

(60) Provisional application No. 60/794,634, filed on Apr. 25, 2006.

(51) Int. Cl.
*A61F 2/06* (2006.01)
*A61F 2/24* (2006.01)
(52) U.S. Cl. ...... 623/1.24; 623/1.26; 623/2.1; 623/2.17; 623/2.18
(58) Field of Classification Search .................. 623/1.24, 623/2.1–2.19, 1.42–1.43
See application file for complete search history.

(56) References Cited

U.S. PATENT DOCUMENTS

| | | | |
|---|---|---|---|
| 5,234,456 A | 8/1993 | Silvestrini | 623/1.2 |
| 5,380,299 A | 1/1995 | Fearnot et al. | 604/265 |
| 5,609,629 A | 3/1997 | Fearnot et al. | 623/1.42 |
| 5,824,048 A | 10/1998 | Tuch | 128/898 |
| 5,873,904 A | 2/1999 | Ragheb et al. | 623/1.13 |
| 5,891,108 A | 4/1999 | Leone et al. | 604/264 |
| 6,096,070 A | 8/2000 | Ragheb et al. | 623/1.39 |
| 6,299,604 B1 | 10/2001 | Ragheb et al. | 604/265 |
| 6,508,833 B2 | 1/2003 | Pavcnik et al. | 623/1.15 |
| 6,530,951 B1 | 3/2003 | Bates et al. | 623/1.45 |
| 6,599,275 B1 | 7/2003 | Fischer, Jr. | 604/265 |
| 6,730,064 B2 | 5/2004 | Ragheb et al. | 604/265 |
| 6,774,278 B1 | 8/2004 | Ragheb et al. | 623/1.1 |
| 6,918,927 B2 | 7/2005 | Bates et al. | 623/1.15 |
| 2002/0111590 A1 | 8/2002 | Davila et al. | 604/265 |
| 2003/0028243 A1 | 2/2003 | Bates et al. | 623/1.15 |
| 2003/0028244 A1 | 2/2003 | Bates et al. | 623/1.15 |
| 2003/0036794 A1 | 2/2003 | Ragheb et al. | 623/1.15 |
| 2003/0229393 A1 | 12/2003 | Kutryk et al. | 623/1.46 |
| 2004/0047909 A1 | 3/2004 | Ragheb et al. | 424/471 |
| 2004/0068241 A1 | 4/2004 | Fischer, Jr. | 604/265 |
| 2004/0073155 A1* | 4/2004 | Laufer et al. | 604/8 |
| 2004/0073284 A1 | 4/2004 | Bates et al. | 623/1.11 |
| 2004/0215339 A1 | 10/2004 | Drasler et al. | 623/3.1 |
| 2004/0225352 A1 | 11/2004 | Osborne et al. | 623/1.24 |
| 2004/0243225 A1 | 12/2004 | Ragheb et al. | 623/1.24 |
| 2004/0254636 A1 | 12/2004 | Flagle et al. | 623/1.24 |
| 2004/0260389 A1* | 12/2004 | Case et al. | 623/1.24 |
| 2005/0015142 A1 | 1/2005 | Austin et al. | 623/1.24 |
| 2005/0182483 A1 | 8/2005 | Osborne et al. | 623/1.24 |
| 2005/0222677 A1 | 10/2005 | Bates et al. | 623/1.42 |
| 2005/0228486 A1 | 10/2005 | Case et al. | 623/1.24 |
| 2005/0278021 A1 | 12/2005 | Bates et al. | 623/1.44 |
| 2006/0047338 A1* | 3/2006 | Jenson et al. | 623/2.11 |
| 2006/0111773 A1* | 5/2006 | Rittgers et al. | 623/1.24 |

* cited by examiner

*Primary Examiner* — Christopher D Koharski
*Assistant Examiner* — Jason-Dennis Stewart
(74) *Attorney, Agent, or Firm* — Buchanan Nipper (57) ABSTRACT

The invention relates to a prosthetic valve for regulating flow through a body lumen and delivering a therapeutic agent into said lumen. In one embodiment, the prosthesis includes a frame having an exterior wall, a hollow interior space, a valve member, and at least one aperture through the exterior wall that permits a controlled amount of therapeutic agent loaded into the hollow interior into the surrounding body lumen following implantation. In another embodiment, the prosthesis includes a frame having a groove, a valve member, and therapeutic agent loaded in the groove.

20 Claims, 8 Drawing Sheets

ARTIFICIAL VENOUS VALVE CONTAINING THERAPEUTIC AGENT

RELATED APPLICATIONS

This application claims the benefit of provisional U.S. Patent Application Ser. No. 60/794,634, filed Apr. 25, 2006, which is incorporated herein by reference in its entirety.

TECHNICAL FIELD

The present invention relates to medical devices for implantation in a body vessel. More particularly, the present invention relates to intraluminal valve prostheses with thromboresistant properties. The invention further describes methods for the local administration of therapeutic agents to a target site.

BACKGROUND

The venous system includes a multitude of one-way bicuspid valves that permit substantially unidirectional blood to flow toward the heart. These valves are particularly important in the lower extremities to prevent the pooling of blood. When the leaflets of the bicuspid valves fail to close properly, the valve is considered "incompetent" as it permits leakage of retrograde flow resulting in the abatement of flow towards the heart.

This potentially serious condition is known as "chronic venous insufficiency." Symptoms can progress from unsightly "spider" or varicose veins to skin discoloration and painful skin ulcerations. The etiology of venous insufficiency is multifactorial, including a past history of thrombotic events, chronic venous stasis, and venous hypertension. Current treatments for venous insufficiency include elevation of the feet and compression stockings. While these can relieve symptoms, the underlying disease remains untreated. Surgical techniques are also employed in which native valves can be bypassed or replaced with autologous sections of veins having functioning valves.

Minimally invasive techniques and instruments for placement of intraluminal medical devices have been developed to treat and repair undesirable conditions within body vessels, including treatment of conditions that affect blood flow such as venous insufficiency. Recently, prosthetic valves implantable via intraluminal transcatheter delivery systems have been developed. However, post-implantation thrombosis and platelet deposition on surfaces of endovascular prosthetic valves may occlude the conduit defined by the endovascular prosthesis or compromise the function of an implanted valve by limiting the motion or responsiveness of moveable portions of the device such as valve leaflets.

To prevent such occlusion, prosthetic valves may be implanted in combination with therapeutic agents. For example, a therapeutic agent may be locally administered through a catheter positioned within the body vessel near the prosthesis, or by coating the prosthesis with the therapeutic agent. Unfortunately, such methods and coated prostheses have not been completely effective in preventing impaired valve function due to the short time interval over which the therapeutic agent is delivered to the site of implantation.

SUMMARY

The present invention relates to an implantable prosthetic valve for regulating fluid flow through a body vessel and delivering a therapeutic agent in the area surrounding implantation.

In one embodiment of the present invention, the prosthetic valve comprises a frame having an exterior wall which defines a hollow interior space, and at least one aperture defining a conduit through the exterior wall. A valve member adapted to modify fluid flow through a body lumen is operatively connected to the exterior wall. The hollow interior space is loaded with therapeutic agent such that at least a portion thereof may pass through the aperture. The apertures provide for the delivery of therapeutic agent to the vessel lumen following implantation and optimally control the therapeutic agent elution rate. Desirably, the therapeutic agent is thromboresistant or thrombolytic. Even more desirable, the therapeutic agent is heparin or hirudin.

In another embodiment, the medical device comprises a frame and a valve member. The frame contains a groove, which is loaded with therapeutic agent. Desirably, the therapeutic agent is thromboresistant or thrombolytic. Even more desirable, the therapeutic agent is heparin or hirudin.

In a further embodiment, a method of treating valvular insufficiency is provided. The method comprises providing a valve prosthesis comprising a frame loaded with therapeutic agent and impaling the prosthesis into a patient in need thereof.

DETAILED DESCRIPTION

The present invention provides for the release of a therapeutic agent from a prosthetic valve implanted within a body passage. The implantable prosthesis comprises one or more therapeutic agents. Preferably, the therapeutic agent is thromboresistant and/or thrombolytic. The implantable prosthesis can have any suitable configuration to perform a desired function, but preferably is adapted for implantation in a vein or within a heart.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The term "implantable" refers to an ability of a medical device to be positioned at a location within a body, such as within a body lumen.

The term "frame" as used herein refers to a structure that can be implanted, or adapted for implantation, within the lumen of a body vessel.

As used herein, the term "body vessel" means any tube-shaped body passage lumen that conducts fluid, including but not limited to blood vessels such as those of the human vasculature system, esophageal, intestinal, billiary, urethral and ureteral passages.

The terms "about" or "substantially" used with reference to a quantity includes variations in the recited quantity that are equivalent to the quantity recited, such as an amount that is insubstantially different from a recited quantity for an intended purpose or function.

As used herein, the phrase "therapeutic agent" refers to any pharmaceutically active agent that results in an intended therapeutic effect on the body to treat or prevent conditions or diseases. Therapeutic agents include any suitable biologically active chemical compounds, biologically derived components such as cells, peptides, antibodies, and polynucleotides, and radiochemical therapeutic agents, such as radioisotopes.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "alloy" refers to a substance composed of two or more metals or of a metal and a nonmetal intimately united, for example by chemical or physical interaction. Alloys can be formed by various methods, including being fused together and dissolving in each other when molten, although molten processing is not a requirement for a material to be within the scope of the term "alloy." As understood in the art, an alloy will typically have physical or chemical properties that are different from its components.

Prosthetic Valve

A prosthetic valve according to the present invention comprises a frame, a therapeutic agent, and a valve member for regulating fluid through a body vessel. The prosthetic valve may be any prosthesis that is introduced temporarily or permanently into the body for the prophylaxis or therapy of a medical condition. For example, such medical devices may include, but are not limited to, heart valve prostheses, venous valve prostheses, artificial organs such as artificial hearts, and ventricular assist devices. Typical subjects (also referred to herein as "patients") are vertebrate subjects (i.e., members of the subphylum cordata), including, mammals such as cattle, sheep, pigs, goats, horses, dogs, cats and humans.

Implantable Frame Having Hollow Interior Space

A wide variety of frames having a hollow interior space are known in the medical technology arts, and any suitable hollow frame can be utilized. For example, in one embodiment of the present invention, the implantable frame comprises a frame with an exterior wall defining a hollow interior space, and at least on or more apertures formed in the frame exterior surface defining a conduit from the frame exterior to the frame hollow interior space. The hollow interior space is loaded with a therapeutic agent. The frame interior space may be continuous through the whole prosthesis, or, alternatively, if the frame interior space is discontinuous, the frame interior space ends may be sealed. Desirably, the frame interior space is loaded with a therapeutic agent. Even more desirably, both the frame interior space and frame apertures are loaded with a therapeutic agent. To maximize the therapeutic agent that may be loaded, the frame interior space desirably has a diameter as large as possible while retaining the structural integrity of the frame.

The apertures may serve as a mechanism that controls the elution rate of the therapeutic agent. For example, decreasing the size of the apertures generally slows the rate of release of the therapeutic agent contained in the hollow frame interior space. Preferably, the aperture size is between about 0.0001 inches and the maximum permissible aperture size, typically the difference between the frame exterior wall thickness and the frame's exterior diameter. In some embodiments, frame wall thickness may vary along the length of the hollow frame and thus permit varying maximum permissible aperture sizes. Frame wall thickness is represented by the traverse between the frame hollow interior space surface and frame exterior surface.

When more than one aperture is present, any suitable configuration of apertures may be utilized. The appropriate aperture configuration will depend on the prosthetic valve's intended use. For example, apertures may be oriented in a linear fashion along the longitudinal axis of the frame, linearly along the lateral axis of the frame, in a helical pattern along the frame, in a double helix along the frame, in a zig-zag, randomly, or any combination of the foregoing. Preferably, the apertures are oriented longitudinally along the frame.

Figure 1A:
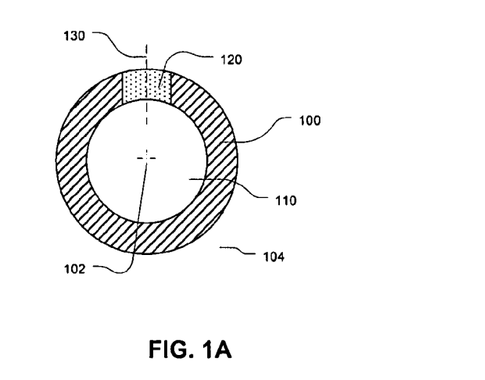
FIGS. 1A, 1B, and 1C are cross-sections of a first preferred embodiment of the present invention.
Figure 1B:
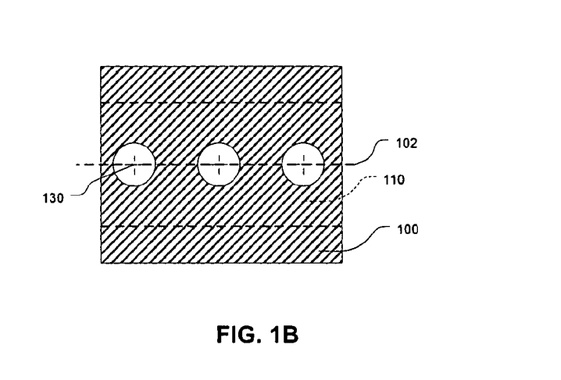
Figure 1C:
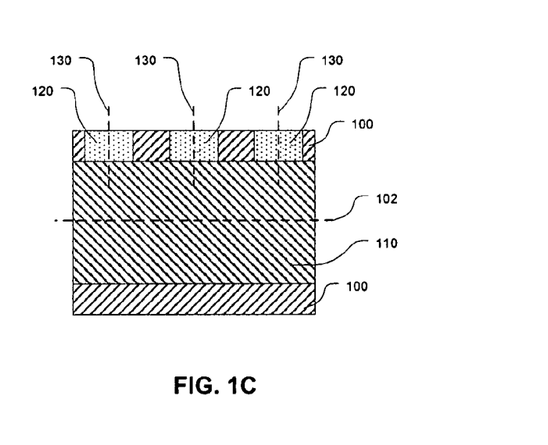
Figure 1D:
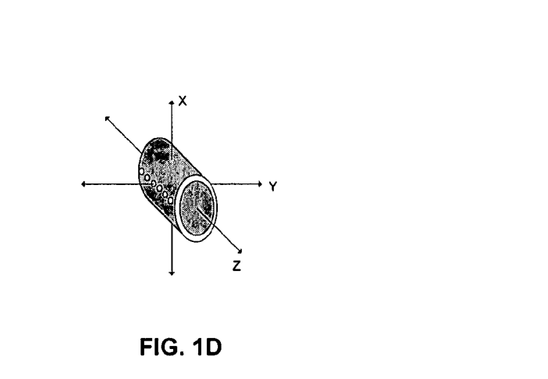
FIG. 1D is a perspective view of the frame of FIGS. 1A-1C.

FIGS. 1A, 1B, and 1C illustrate a frame according to a first embodiment of the present invention. FIG. 1A shows a cross-section of hollow frame segment 100 in the xy plane, shown in FIG. 1D. FIG. 1B is a view in the yz plane of hollow frame segment 100. FIG. 1C is a cross-section of a wall of hollow frame segment 100 in the xz plane. The frame segment 100 includes a hollow interior space 110 oriented about the frame's z-axis 102. Apertures 120 are oriented linearly along the frame's z-axis 102, and define conduits 130 from the frame exterior 104 to the frame interior space 110 through which therapeutic agent may elute. Preferably, the frame interior space 110 is loaded with therapeutic agent. Even more preferably, the apertures 120 are also loaded with therapeutic agent.

Figure 2A:
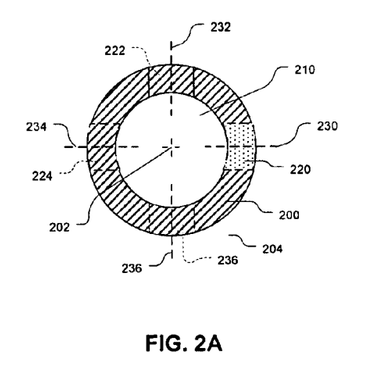
FIGS. 2A, 2B and 2C are cross-sections of another preferred embodiment of the present invention.
Figure 2B:
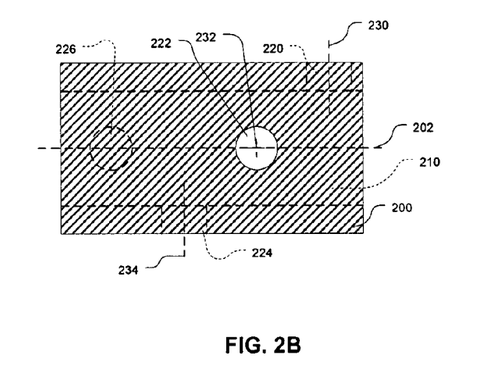
Figure 2C:
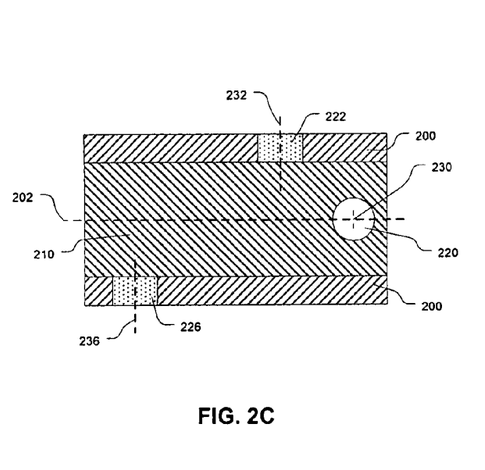
Figure 2D:
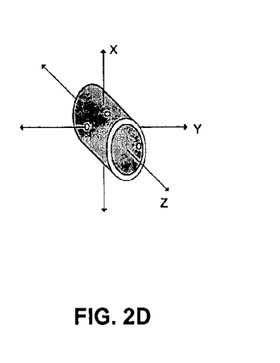
FIG. 2D is a perspective view of the frame of FIGS. 2A-2C.

FIGS. 2A, 2B, and 2C illustrate a frame according to a second embodiment. FIG. 2A shows a cross-section of hollow frame 200 in the xy plane, shown in FIG. 2D. FIG. 2B is a view in the yz plane of hollow frame segment 200. FIG. 2C is a cross-section of a wall of hollow frame segment 200 viewed in the xz plane. The frame segment 200 includes a hollow interior space 210 oriented about the frame's z-axis 202. Apertures 220, 222, 224, and 226 are arranged in a helical pattern about the frame's z-axis 202. The apertures 220, 222, 224, and 226 define conduits 230, 232, 234, and 236, respectively, from the frame exterior 204 to the frame interior space 210. Preferably, the interior space 210 is loaded with therapeutic agent. Even more preferably, apertures 220, 222, and 226 are also loaded with therapeutic agent.

Figure 3A:
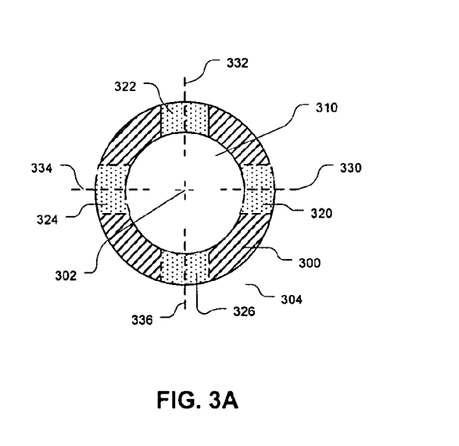
FIGS. 3A, 3B and 3C are cross-sections of yet another preferred embodiment of the present invention.
Figure 3B:
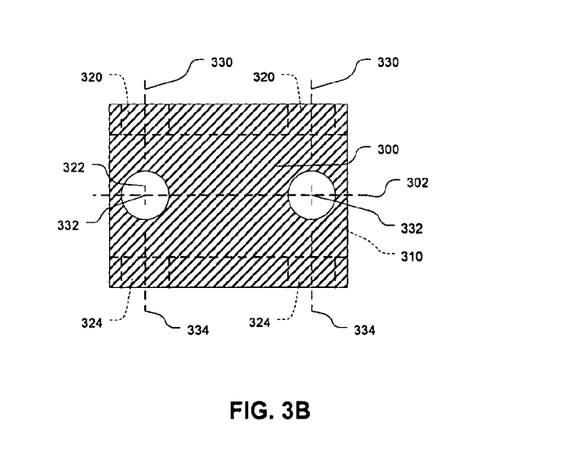
Figure 3C:
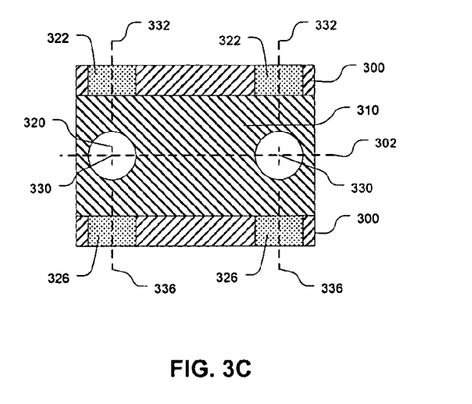
Figure 3D:
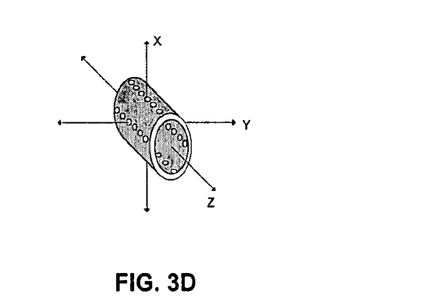
FIG. 3D is a perspective view of the frame of FIGS. 3A-3C.

FIGS. 3A, 3B, and 3C illustrate a frame according to a third embodiment. FIG. 3A shows a cross-section of a hollow prosthesis frame 300 in the xy plane, shown in FIG. 3D. FIG. 3B is a view in the yz plane of hollow prosthesis frame segment 300. FIG. 3C is a cross-section of a wall of hollow frame segment 300 in the xz plane. The frame segment 300 includes a hollow interior space 310 oriented about the frame's z-axis 302. Apertures 320, 322, 324, and 326 are arranged about the frame's y-axis. The apertures 320, 322, 324, and 326 define conduits 330, 332, 334, and 336, respectively, from the frame exterior 304 to the frame interior space 310. Preferably, the interior space 310 is loaded with therapeutic agent. Even more preferably, apertures 320, 322, 324, and 326 are also loaded with therapeutic agent.

In another embodiment of the present invention, the implantable frame comprises a groove for containing the therapeutic agent. The groove may function to increase the elution rate of therapeutic agent contained there within. The groove may be oriented in any possible manner along the frame. For example, the groove may run linearly along the longitudinal axis of the frame, in a helix, and in a zig-zag. Preferably, the groove is aligned with the longitudinal axis of the frame. The groove may be of any possible depth.

Figure 4A:
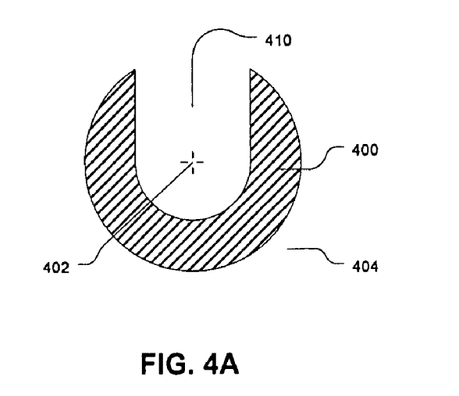
FIGS. 4A and 4B are cross-sections of a further preferred embodiment of the present invention.
Figure 4B:
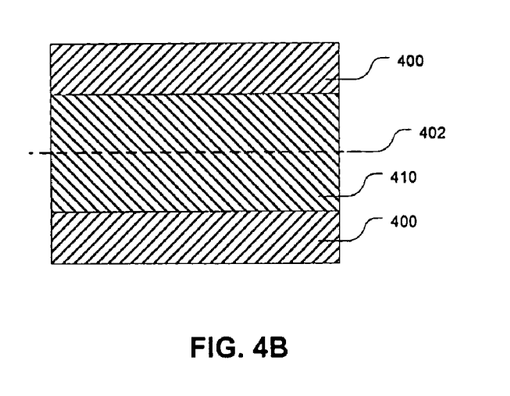
Figure 4C:
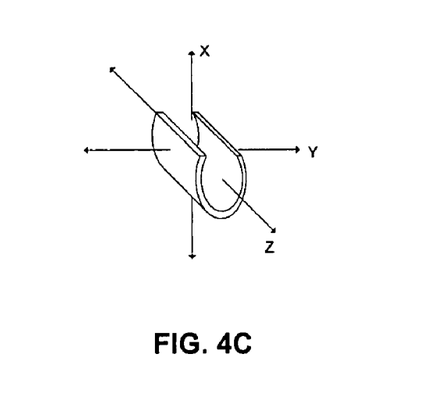
FIG. 4C is a perspective view of the frame of FIGS. 4A-4B.

FIGS. 4A and 4B illustrate a frame according to a fourth embodiment. FIG. 4A is a cross-section of a grooved prosthesis frame 400 in the xy plane, shown in FIG. 4C. FIG. 4B is a view in the yz plane of the grooved prosthesis segment 400. The frame segment 400 includes a groove 410 running along the frame's z-axis 402. Preferably, the groove 410 is loaded with therapeutic agent that may elute to the frame exterior 404.

Suitable frames can have a variety of configurations, including braided strands, helically wound strands, ring members, consecutively attached ring members, and zig-zag members. Also, suitable frames can have a variety of sizes. The exact configuration and size chosen will depend on several factors, including the desired delivery technique, the nature of the vessel in which the device will be implanted, and the size of the vessel.

A frame structure and configuration can be chosen to facilitate maintenance of the device in the vessel following implantation. For example, frame material that is too stiff can damage the vessel, not conform well to the vessel wall, and increase the profile of the device when loaded in a delivery system prior to deployment. Frame material that is not sufficiently stiff may not allow the valve leaflet to function as desired.

Preferably, the frame has a compressed and an expanded configuration. In some embodiments, the expanded configuration may be resiliently further extended in one or more radial directions. In some embodiments, a frame can expand from a compressed, or unexpanded, delivery configuration to one or more radially expanded deployment configurations, for example through self-expansion or balloon-expansion of the frame. The expanded configuration can have any suitable cross-sectional configuration, including circular or elliptical.

In one embodiment, the frame can be oriented along the longitudinal axis of a body vessel in the expanded or compressed configurations.

In one embodiment, the frame is self-expanding. Upon compression, self-expanding frames can expand toward their pre-compression geometry. In some embodiments, a self-expanding frame can be compressed into a low-profile delivery conformation and then constrained within a delivery system for delivery to a point of treatment in the lumen of a body vessel. At the point of treatment, the self-expanding frame can be released and allowed to subsequently expand to another configuration.

In other embodiments the frames are not self-expanding, or are balloon expandable.

The dimensions of the implantable frame will depend on its intended use. Typically, the collapsed dimension of the frame will usually be in the range from about 1 mm to 10 mm, more usually being in the range from 1.5 mm to 6 mm for vascular applications. The expanded dimension will usually be in the range from about 2 mm to about 30 mm, preferably being in the range from about 2.5 mm to about 18 mm for vascular applications.

The frame can include structural features, such as barbs, that maintain the frame in position following implantation in a body vessel. The art provides a wide variety of structural features that are acceptable for use in the medical device, and any suitable structural feature can be used. Furthermore, barbs can also comprise separate members attached to the frame by suitable attachment means, such as welding and bonding. For instance, barbs can be formed by V-shaped cuts transversing the thickness of a flat metal frame, which are bent outward to form the barb. In some embodiments, the number, arrangement, and configuration of the integral barbs can vary according to design preference and the clinical use of the device. The barbs can have any suitable shape, including points or "fish hook"-like configurations. The barbs may or may not penetrate the vein wall, depending on their design and other factors, including the thickness and type of covering used.

Also provided are embodiments wherein the frame comprises a means for orienting the frame within a body lumen. For example, the frame can comprise a marker, such as a radiopaque portion of the frame that would be seen by remote imaging methods including X-ray, ultrasound, Magnetic Resonance Imaging and the like, or by detecting a signal from or corresponding to the marker. In other embodiments, the delivery device can comprise a frame with indicia relating to the orientation of the frame within the body vessel. In other embodiments, indicia can be located, for example, on a portion of a delivery catheter that can be correlated to the location of the frame within a body vessel.

A frame or delivery device may comprise one or more radiopaque materials to facilitate tracking and positioning of the medical device, which may be added in any fabrication method or absorbed into or sprayed onto the surface of part or all of the medical device. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and anti-microbial properties. Radiopacity is typically determined by fluoroscope or x-ray film.

Suitable frames may be made from one or more suitable materials and need only be biocompatible or able to be made biocompatible. Examples of suitable materials include, without limitation, stainless steel, nitinol, MP35N, gold, tantalum, platinum or platinum iridium, niobium, tungsten, inconel, ceramic, nickel, titanium, stainless steel/titanium composite, cobalt, chromium, cobalt/chromium alloys, magnesium, aluminum, or other biocompatible metals and/or composites or alloys such as carbon or carbon fiber, cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene teraphthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the frame material includes stainless steel or nitinol.

Valve Members

Prosthetic valves according to the present invention comprise at least one valve member. Prosthetic valves comprising at least one valve member can be used to regulate fluid flow in a vein, for example, to treat venous valve incompetency. For example, one or more prosthetic valves comprising one or more valve members can be implanted in a vein with incompetent native venous valves so as to provide a valve to replace the incompetent native valves therein.

A valve member, according to some embodiments, can comprise a leaflet comprising a free edge responsive to the flow of fluid through the body vessel. A "free edge" refers to a portion of a leaflet that is not attached to the prosthetic valve, but forms a portion of a valve orifice. Preferably a leaflet free edge is a portion of the edge of the leaflet that is free to move in response to the direction of fluid flow in contact with the leaflet. A valve leaflet is one type of valve member. Preferably, one or more valve members attached to a prosthetic valve can permit fluid to flow through a body vessel in a first direction while substantially preventing fluid flow in the opposite direction.

A wide variety of materials acceptable for use as valve members are known in the art, and any suitable material can be utilized. The material chosen need only be able to perform as described herein, and be biocompatible, or able to be made biocompatible. Examples of suitable materials include flexible materials, natural materials, and synthetic materials. Examples of suitable natural materials include collagen and extracellular matrix (ECM) material, such as submucosa. Small intestine submucosa (SIS) is particularly well-suited for use as valve members, such as leaflets. Examples of suitable polymeric materials include polyesters, such as poly (ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers on the material surface, coating of the surface with a crosslinked biocompatible polymer, chemical modification with biocompatible functional groups, and immobilization of a compatibilizing agent such as heparin or other substances.

Desirably, the valve member is made of one or more polymers that do not require treatment or modification to be biocompatible. More desirably, the valve member includes a biocompatible polyurethane. One example of a biocompatible polyurethane, THORALON (THORATEC, Pleasanton, Calif.), has been used in certain vascular applications and is characterized by thromboresistance, high-tensile strength, low-water absorption, low-critical surface tension and good flex life. THORALON and methods of manufacturing this material are disclosed in U.S. Pat. Application Publication No. 2002/0065552 A1 and U.S. Pat. Nos. 4,861,830 and 4,675,361, each of which is incorporated herein by reference in its entirety. Accordingly, THORALON is a polyurethane based polymer (referred to as BPS-215) blended with a siloxane-containing surface modifying additive (referred to as SMA-300). Base polymers containing urea linkages can also be used. The concentration of the surface modifying additive may be in the range of 0.5% to 5% by weight of the base polymer.

THORALON can be manipulated to provide either a porous or non-porous material. Formation of porous THORALON is described, for example, in U.S. Pat. No. 6,752,826 and U.S. Pat. Appl. No. 2003/0149471 A1, both of which are incorporated herein by reference in their entirety. The pores in the polymer may have an average pore diameter from about 1 micron to about 400 microns. Preferably the average pore diameter is from about 1 micron to about 100 microns, and more preferably is from about 1 micron to about 10 microns.

A variety of other biocompatible polyurethanes/polycarbamates and urea linkages (hereinafter "—C(O)N or CON type polymers") may also be employed. Biocompatible CON type polymers modified with cationic, anionic and aliphatic side chains may also be used. See, for example, U.S. Pat. No. 5,017,664, which is incorporated herein by reference in its entirety.

Other biocompatible CON type polymers include: segmented polyurethanes, such as BIOSPAN; polycarbonate urethanes, such as BIONATE; polyetherurethanes, such as ELASTHANE; (all available from POLYMER TECHNOLOGY GROUP, Berkeley, Calif.); siloxane-polyurethanes, such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes, such as PUR-SIL-10, -20, and -40 TSPU; Polyzene-F and polyphosphazene fluropolymers; PTMO and PDMS polyether-based aliphatic siloxane-polyurethanes, such as PUR-SIL AL-5 and AL-10 TSPU; aliphatic, hydroxy-terminated polycarbonate and PDMS polycarbonate-based siloxane-polyurethanes, such as CARBOSIL-10, -20, and -40 TSPU (all available from POLYMER TECHNOLOGY GROUP). Examples of siloxane-polyurethanes are disclosed in U.S. Pat. Application Publication No. 2002/0187288 A1, which is incorporated herein by reference in its entirety.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference in its entirety.

The valve members may be applied to the prosthetic valve with any suitable attachment mechanism, such as sutures, dipping, adhesives, bonding, spraying, tissue welding, self-adhesion between regions of the material, chemical adhesion between the valve member and frame, cross-linking, and the like. The attachment mechanism chosen will depend on the nature of the frame and valve members. For example, in a preferred embodiment, the biocompatible polyurethane may be applied as a solution. If necessary, gentle heating and/or agitation, such as stirring, may be employed to cause substantial dissolution.

Although the prosthetic valves in the illustrative figures are shown with valve members having one or two valve leaflets, the valve member may include any suitable number of leaflets. The valve member need only be able to provide the functionality described herein. The specific number chosen will depend on several factors, including the type and configuration of the frame. For example, the valve member may comprise 1, 2, 3, 4, 5, 6, 7, 8, or more leaflets. The leaflets can be arranged in any suitable configuration with respect to one another and the prosthetic valve. For example, a suitable leaflet configuration in addition to the illustrative figures may comprise a duckbill valve, disclosed in U.S. Publication No. 2004/0254636 to Flagle et al. for a Prosthetic Valve with Vessel Engaging Member, herein incorporated by reference in its entirety.

Figure 5A:
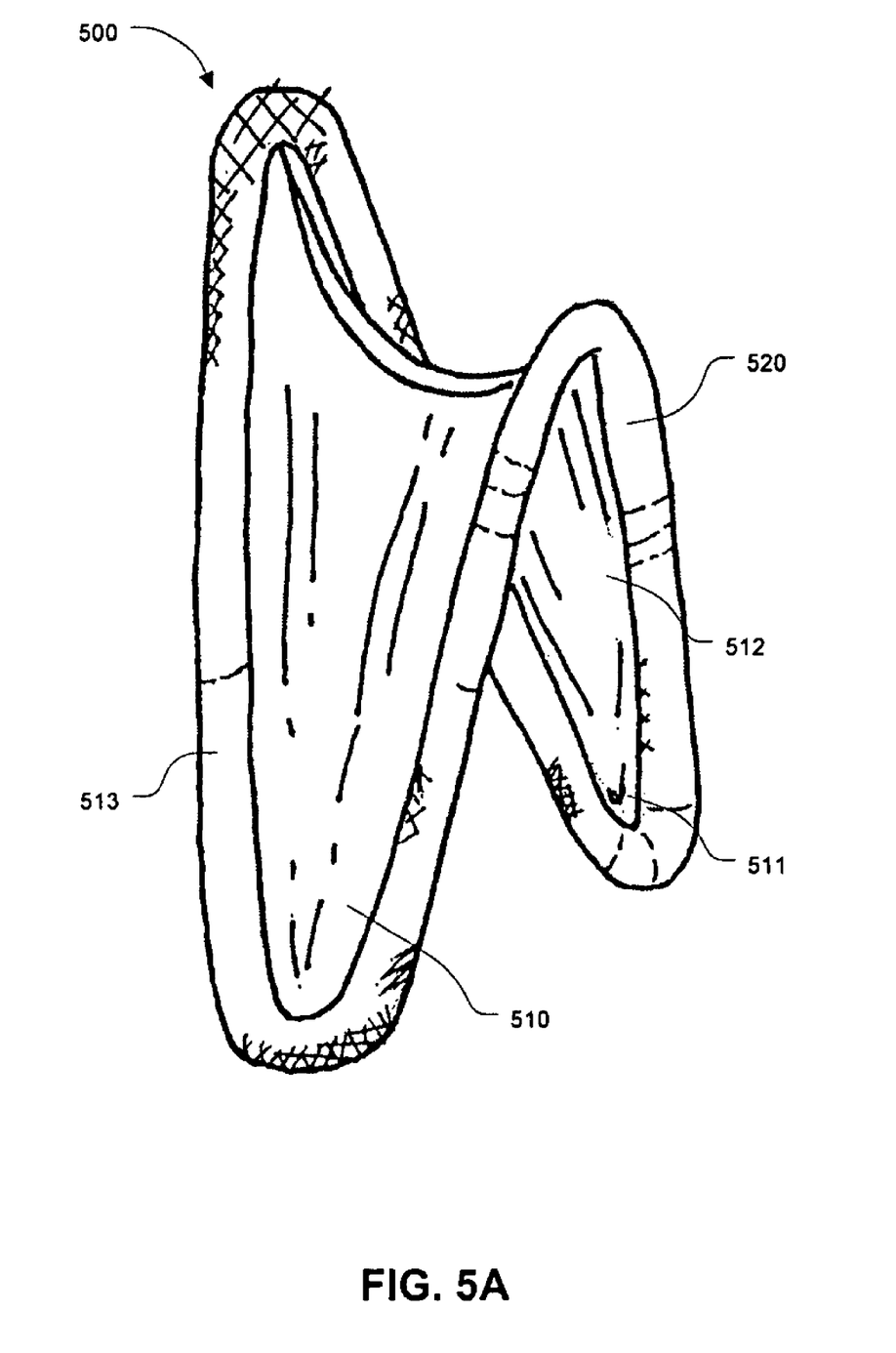
FIG. 5A provides a perspective view of one prosthetic valve of the present invention.
Figure 5B:
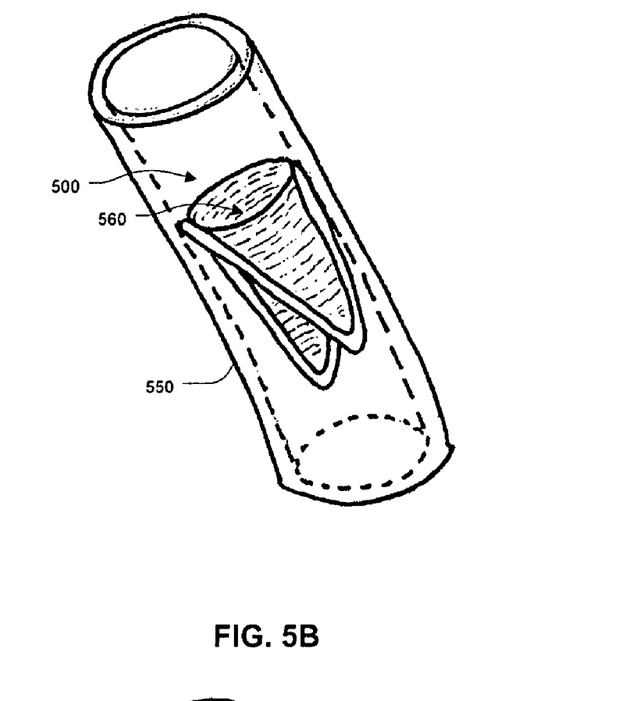
FIGS. 5B and 5C illustrate perspective views of the prosthesis of FIG. 5A implanted within a body lumen.
Figure 7A:
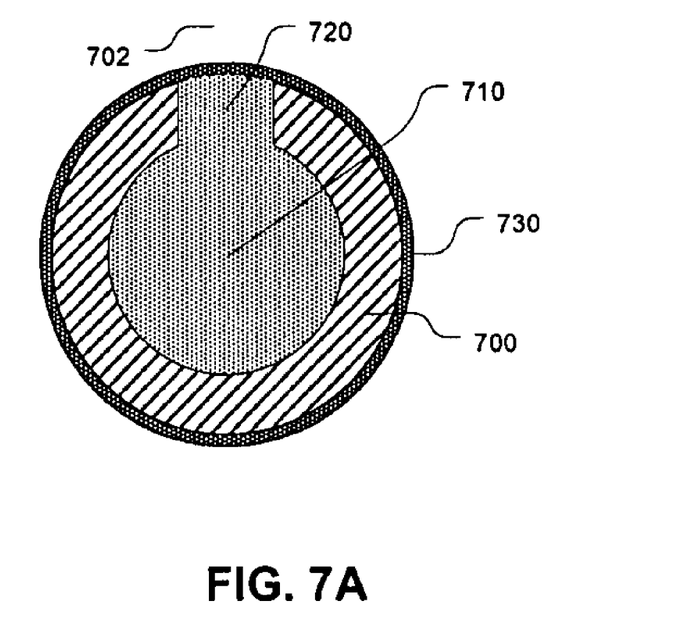
FIGS. 7A and 7B are partially sectioned views of frame segments loaded with therapeutic agent and enveloped in valve material.
Figure 7B:
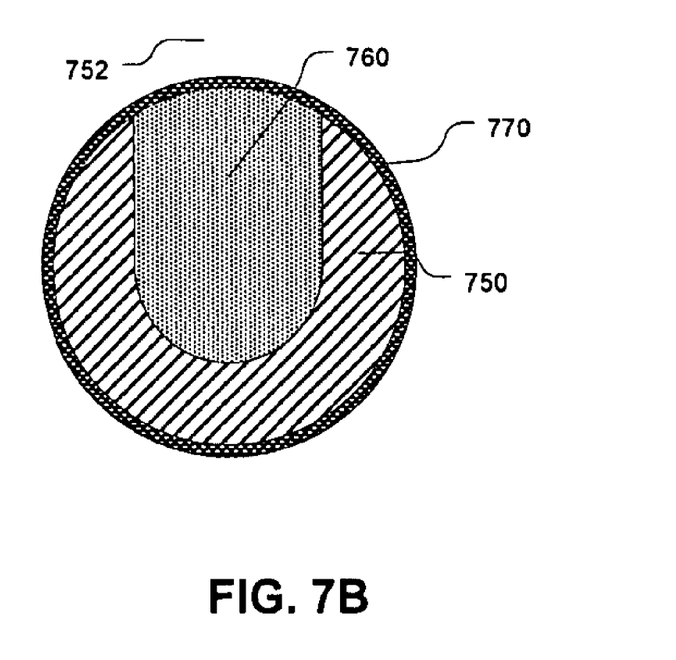

In one preferred embodiment, a valve member can comprise two valve leaflets comprising free edges that may coapt with one another. FIG. 5A is a perspective view of an illustrative prosthetic valve 500, which includes a pair of leaflets 510 attached to the hollow frame 520. The leaflets 510 can be attached to the frame 520 in any suitable manner. For example, in the illustrated embodiment, the leaflets' second ends 511 and sides 512 wrap around the frame exterior 520 such that the leaflets' second segments 513 envelop the frame exterior 520 (as shown in FIGS. 7A and 7B). When the valve 500 is deployed in a body lumen (e.g., at a treatment site within the venous or arterial system), the leaflets 510 move back and forth in response to changes in fluid dynamic pressure. When fluid is stagnant or flowing through the lumen in a normal, forward direction, the leaflets 510 remain mostly open (as shown in FIG. 5B). When fluid begins to flow in a direction opposite its normal, forward flow, the leaflets 510 move toward a closed position (as shown in FIG. 5C).

Figure 5C:
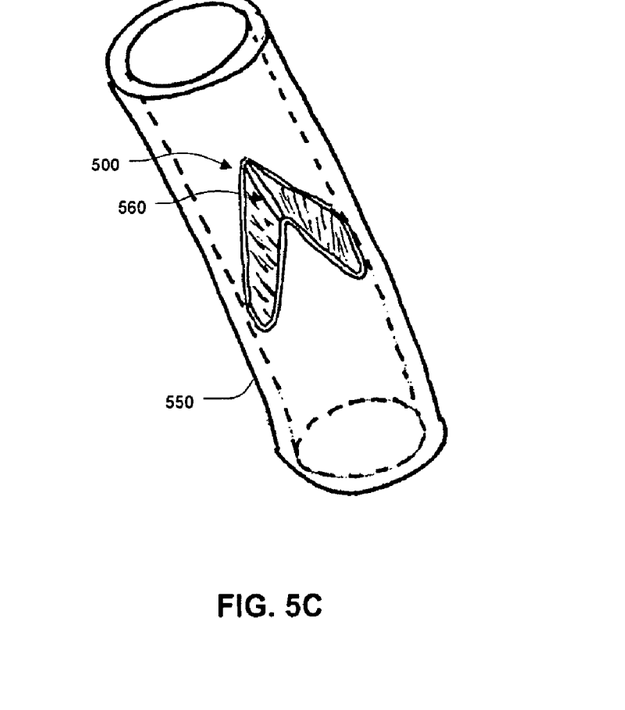

FIGS. 5B and 5C depict certain prosthetic valve configurations for providing valve function in a body lumen. In particular, FIG. 5B provides a perspective view of the valve prosthesis 500 of FIG. 5A implanted within a vascular vessel 550, the valve in a generally open configuration. The prosthetic valve 500 can be attached to the vessel 550 in any suitable manner, including but not limited to those previously described. As depicted, the leaflets 510 are configured to move toward and away from one another to close and open, respectively, the valve orifice 560. FIG. 5C provides a prospective view of the valve of FIG. 5A in a generally closed configuration.

Figure 6A:
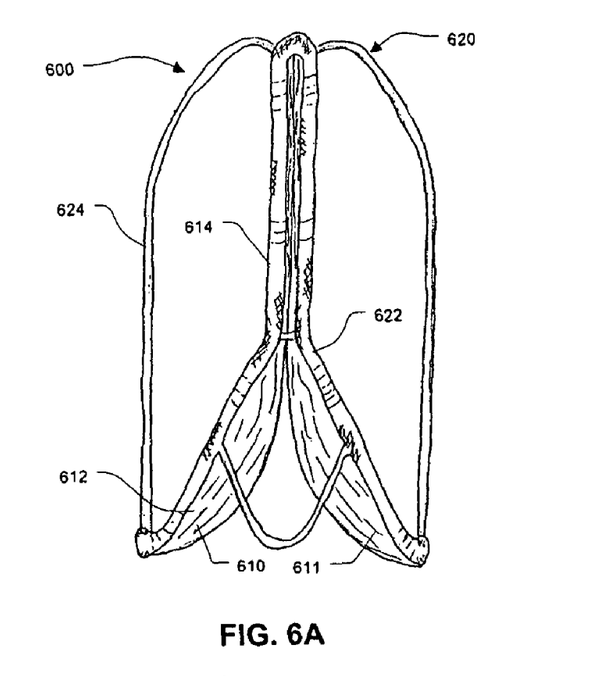
FIGS. 6A and 6B provide perspective views of one prosthetic valve of the invention.
Figure 6B:
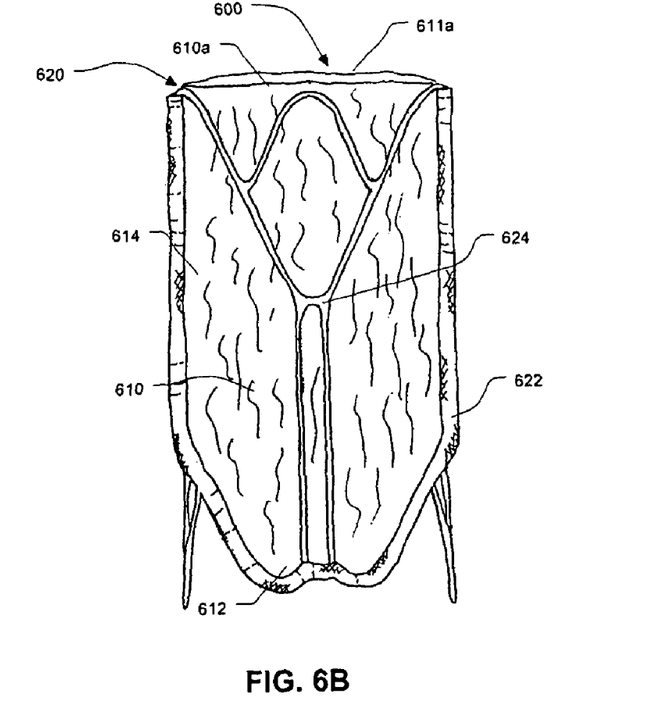

In a further embodiment, the valve member material may only encapsulate a portion of the whole frame. For example, FIGS. 6A and 6B depict various side views of a prosthetic valve 600 of the present invention. Two leaflets 610 and 611 are attached to the frame 620. FIG. 6A provides a side view of prosthetic valve 600 taken in a direction parallel to the coapting upper edges 610a and 611a of leaflets 610 and 611. FIG. 6B shows a view of the prosthesis 600 taken perpendicular to the coapting upper edges 610a and 611a of leaflets 610 and 611. The leaflets second ends 612 and sides 614 wrap around a portion 622 of the frame 620. Frame portion 624 of frame 620 remains uncovered by valve material. The aperture or groove of the frame 620 may be varied depending on whether the frame portion is covered by valve material, such as portion 622, or remains uncovered, such as portion 624, and the desired therapeutic effect.

In one embodiment, the attachment mechanism is such that the valve member material substantially encapsulates the apertures or groove of the frame or a portion of the frame. For example, a porous polyurethane may be sprayed on the support frame such that the polyurethane encapsulates the frame. The porous polyurethane may serve as a barrier that slows the rate of release of the therapeutic agent by providing a medium through which the therapeutic agent must diffuse. The thickness of the polyurethane affects the rate of release of the therapeutic agent from the medical device. Increasing the thickness of the polyurethane generally slows the rate of release of the therapeutic agent(s) from medical device.

FIG. 7A shows a cross-section of a frame of segment 700 according to one embodiment of the present invention. The frame 700 is encapsulated by valve material 730. The frame segment includes a frame interior space 710 and an aperture 720, both loaded with therapeutic agent. The therapeutic agent must elute through the valve material 730 to enable a therapeutic affect about the frame exterior 702. Preferably, the valve material 730 is a porous polymer. Non-porous valve material may be made porous, for example, by cutting pores in the valve material using a laser or heated stylus. Even more preferably, the pores are at least 0.0001 inches wide.

FIG. 7B shows a front view of a frame segment 750 according to another embodiment of the present invention. The frame 750 is encapsulated by valve material 770. The frame segment 750 includes a groove 760 loaded with therapeutic agent. The therapeutic agent must elute through the valve material 770 to enable a therapeutic affect about the frame exterior 752. Preferably, the valve material 770 is a porous polymer. Non-porous valve material may be made porous, for example by cutting pores in the valve material using a laser or heated stylus. Even more preferably, the pores are at least 0.0001 inches wide.

The device can include any suitable number of valve members. The valve members can be arranged in any suitable configuration with respect to one another and the frame. The valve members need only be able to provide the functionality described herein. For example, one or more valve members attached to a frame may, in one embodiment, permit fluid to flow through a body vessel in a first direction while substantially preventing fluid flow in the opposite direction. The specific number chosen will depend on several factors, including the type and configuration of the frame.

Therapeutic Agents

Desirably, implantable valve prostheses comprise a therapeutically effective amount of one or more therapeutic agents in pharmaceutically acceptable salt or ester or prodrug form.

Therapeutic agents that may be used in the present invention include, but are not limited to, pharmaceutically acceptable compositions containing any of the therapeutic agents or classes of therapeutic agents listed herein, as well as any salts and/or pharmaceutically acceptable formulations thereof. Any single therapeutic agent or combination of therapeutic agents may be used in the present invention. Table 1 below provides a non-exclusive list of classes of therapeutic agents and some corresponding exemplary active ingredients.

TABLE 1

| Class | Exemplary Active Ingredients |
|---|---|
| Adrenergic agonist | Adrafinil |
| | Isometheptene |
| | Ephedrine (all forms) |
| Adrenergic antagonist | Monatepil maleate |
| | Naftopidil |
| | Carvedilol |
| | Moxisylyte HCl |
| Adrenergic - Vasoconstrictor/Nasal decongestant | Oxymetazoline HCl |
| | Norfenefrine HCl |
| | Bretylium Tosylate |
| Adrenocorticotropic hormone | Corticotropin |
| Analgesic | Bezitramide |
| | Acetylsalicysalicylic acid |
| | Propanidid |
| | Lidocaine |
| | Pseudophedrine hydrochloride |
| | Acetaminophen |
| | Chlorpheniramine Maleate |
| Anesthetics | Dyclonine HCl |
| | Hydroxydione Sodium |
| | Acetamidoeugenol |
| Anthelmintics | Niclosamide |
| | Thymyl N-Isoamylcarbamate |
| | Oxamniquine |
| | Nitroxynil N-ethylglucamine |
| | Anthiolimine |
| | 8-Hydroxyquinoline Sulfate |
| Anti-inflammatory | Bendazac |
| | Bufexamac |
| | Desoximetasone |
| | Amiprilose HCl |
| | Balsalazide Disodium Salt |
| | Benzydamine HCl |
| Antiallergic | Fluticasone propionate |
| | Pemirolast Postassium salt |
| | Cromolyn Disodium salt |
| | Nedocromil Disodium salt |
| Antiamebic | Cephaeline |
| | Phanquinone |
| | Thiocarbarsone |
| Antianemic | Folarin |
| | Calcium folinate |
| Antianginal | Verapamil |
| | Molsidomine |
| | Isosorbide Dinitrate |
| | Acebutolol HCl |
| | Bufetolol HCl |
| | Timolol Hydrogen maleate salt |
| Antiarryhythmics | Quinidine |
| | Lidocaine |
| | Capobenic Acid |
| | Encainide HCl |
| | Bretylium Tosylate |
| | Butobendine Dichloride |
| Antiarthritics | Azathioprine |
| | Calcium 3-aurothio-2-propanol-1-sulfate |
| | Glucosamine Beta Form |
| | Actarit |
| Antiasthmatics/Leukotriene antagonist | Cromalyn Disodium |
| | Halamid |
| | Montelukast Monosodium salt |
| Antibacterial | Cefoxitin Sodium salt |
| | Lincolcina |
| | Colisitin sulfate |
| Antibiotics | Gentamicin |
| | Erythromycin |
| | Azithromycin |
| Anticoagulants | Heprin sodium salt |
| | Heprinar |
| | Dextran Sulfate Sodium |
| Anticonvulsants | Paramethadione |
| | Phenobarbital sodium salt |
| | Levetiracetam |
| Antidepressants | Fluoxetine HCl |
| | Paroxetine |
| | Nortiptyline HCl |

TABLE 1-continued

| Class | Exemplary Active Ingredients |
|---|---|
| Antidiabetic | Acarbose |
| | Novorapid |
| | Diabex |
| Antiemetics | Chlorpromazine HCl |
| | Cyclizine HCl |
| | Dimenhydrinate |
| Antiglaucoma agents | Dorzolamide HCl |
| | Epinepherine (all forms) |
| | Dipivefrin HCl |
| Antihistamines | Histapyrrodine HCl |
| Antihyperlipoproteinemic | Lovastatin |
| | Pantethine |
| Antihypertensives | Atenolol |
| | Guanabenz Monoacetate |
| | Hydroflumethiazide |
| Antihyperthyroid | Propylthiouracil |
| | Iodine |
| Antihypotensive | Cortensor |
| | Pholedrine Sulfate |
| | Norepinephrine HCl |
| Antineoplastic | 9-Aminocamptothecin |
| | Carboquone |
| | Benzodepa |
| | Bleomycins |
| | Capecitabine |
| | Doxorubicin HCl |
| Antiperistaltic; antidiarrheal | Bismuth Subcarbonate |
| | Bismuth Subsalicylate |
| | Mebiquine |
| | Diphenoxylate HCl |
| Antiprotozoal | Fumagillin |
| | Melarsoprol |
| | Nitazoxanide |
| | Aeropent |
| | Pentamideine Isethionate |
| | Oxophenarsine Hydrochloride |
| Antipyretics | Dipyrocetyl |
| | Naproxen |
| | Tetrandrine |
| | Imidazole Salicylate |
| | Lysine Acetylsalicylate |
| | Magnesium Acetylsalicylate |
| Antirheumatic | Auranofin |
| | Azathioprine |
| | Myoral |
| | Penicillamine HCl |
| | Chloroquine Diphosphate |
| | Hydroxychloroquine Sulfate |
| Antispasmodic | Ethaverine |
| | Octaverine |
| | Rociverine |
| | Ethaverine HCl |
| | Fenpiverinium Bromide |
| | Leiopyrrole HCl |
| Antithrombotic | Plafibride |
| | Triflusal |
| | Sulfinpyrazone |
| | Ticlopidine HCl |
| Antitussives | Anethole |
| | Hydrocodone |
| | Oxeladin |
| | Amicibone HCl |
| | Butethamate Citrate |
| | Carbetapentane Citrate |
| Antiulcer agents | Polaprezinc |
| | Lafutidine |
| | Plaunotol |
| | Ranitidine HCl |
| | Pirenzepine 2 HCl |
| | Misoprostol |
| Antiviral agents | Nelfinavir |
| | Atazanavir |
| | Amantadine |
| | Acyclovir |
| | Rimantadine HCl |
| | Epivar |
| | Crixivan |

TABLE 1-continued

| Class | Exemplary Active Ingredients |
|---|---|
| Anxiolytics | Alprazolam |
| | Cloxazolam |
| | Oxazolam |
| | Flesinoxan HCl |
| | Chlordiazepoxide HCl |
| | Clorazepic Acid Dipotassium salt |
| Bronchodilator | Epinephrine |
| | Theobromine |
| | Dypylline |
| | Eprozinol 2HCl |
| | Etafedrine |
| Cardiotonics | Cymarin |
| | Oleandrin |
| | Docarpamine |
| | Digitalin |
| | Dopamine HCl |
| | Heptaminol HCl |
| Cholinergic | Eseridine |
| | Physostigmine |
| | Methacholine Chloride |
| | Edrophonium chloride |
| | Juvastigmin |
| Cholinergic antagonist | Pehencarbamide HCl |
| | Glycopyrrolate |
| | Hyoscyamine Sulfate dihydrate |
| Cognition enhancers/Nootropic | Idebenone |
| | Tacrine HCl |
| | Aceglutamide Aluminum Complex |
| | Acetylcarnitine L HCl |
| Decongestants | Propylhexedrine dl-Form |
| | Pseudoephedrine |
| | Tuaminoheptane |
| | Cyclopentamine HCL |
| | Fenoxazoline HCl |
| | Naphazoline HCl |
| Diagnostic aid | Disofenin |
| | Ethiodized Oil |
| | Fluorescein |
| | Diatrizoate sodium |
| | Meglumine Diatrizoate |
| Diuretics | Bendroflumethiazide |
| | Fenquizone |
| | Mercurous Chloride |
| | Amiloride HCl 2 $H_2O$ |
| | Manicol |
| | Urea |
| Enzyme inhibitor (proteinase) | Gabexate Methanesulfonate |
| Fungicides | Candicidin |
| | Filipin |
| | Lucensomycin |
| | Amphotericin B |
| | Caspofungin Acetate |
| | Viridin |
| Gonad stimulating principle | Clomiphene Citrate |
| | Chorionic gonadotropin |
| | Humegon |
| | Luteinizing hormone (LH) |
| Hemorheologic agent | Poloxamer 331 |
| | Azupentat |
| Hemostatic | Hydrastine |
| | Alginic Acid |
| | Batroxobin |
| | 6-Aminohexanoic acid |
| | Factor IX |
| | Carbazochrome Salicylate |
| Hypolimpemic agents | Clofibric Acid Magnesium salt |
| | Dextran Sulfate Sodium |
| | Meglutol |
| Immunosuppresants | Azathioprine |
| | 6-Mercaptopurine |
| | Prograf |
| | Brequinar Sodium salt |
| | Gusperimus Trihydrochloride |
| | Mizoribine |
| | Rapamycin and analogs thereof |
| Mydriatic; antispasmodic | Epinephrine |
| | Yohimbine |
| | Aminopentamide dl-Form |
| | Atropine Methylnitrate |
| | Atropine Sulfatemonohydrate |
| | Hydroxyamphetamine (I, HCl, HBr) |
| Neuromuscular blocking agent/ Muscle relaxants (skeletal) | Phenprobamate |
| | Chlorzoxazone |
| | Mephenoxalone |
| | Mioblock |
| | Doxacurium Chloride |
| | Pancuronium bromide |
| Oxotocic | Ergonovine Tartrate hydrate |
| | Methylergonovine |
| | Prostaglandin $F_{2\alpha}$ |
| | Intertocine-S |
| | Ergonovine Maleate |
| | Prostoglandin $F_{2\alpha}$ Tromethamine salt |
| Protease | Elastase |
| | Cathepsin G |
| Radioprotective agent | Amifostine $3H_2O$ |
| Sedative/Hypnotic | Haloxazolam |
| | Butalbital |
| | Butethal |
| | Pentaerythritol Chloral |
| | Diethylbromoacetamide |
| | Barbital Sodium salt |
| Serenic | Eltoprazine |
| Thrombolytic | Alteplase, Recombinant |
| | Anistreplase |
| | Reteplase, Recombinant |
| | Streptokinase |
| | Urokinase |
| Tocolytic agents | Albuterol Sulfate |
| | Terbutaline sulfate |
| Treatment of cystic fibrosis | Uridine 5'-Triphosphate Trisodium dihydrate salt |
| Vasoconstrictor | Nordefrin (−) Form |
| | Propylhexedrine dl-form |
| | Nordefrin HCl |
| Vasodilators | Nylidrin HCl |
| | Papaverine |
| | Erythrityl Tetranitrate |
| | Pentoxifylline |
| | Diazenium diolates |
| | Citicoline |
| | Hexestrol |
| | Bis(diethylaminoethyl ether) 2HCl |
| Vitamins | α-Carotene |
| | β-Carotene |
| | Vitamin $D_3$ |
| | Pantothenic Acid sodium salt |

Other desirable therapeutic agents include, but are not limited to, the following: (a) anti-inflammatory/immunomodulators such as dexamethasone, m-prednisolone, interferon g-1b, leflunomide, sirolimus, tacrolimus, everolimus, pimecrolimus, biolimus (such as Biolimus A7 or A9) mycophenolic acid, mizoribine, cyclosporine, tranilast, and viral proteins; (b) antiproliferatives such as paclitaxel or other taxane derivatives (such as QP-2), actinomycin, methothrexate, angiopeptin, vincristine, mitomycine, statins, C MYC antisense, ABT-578, RestenASE, Resten-NG, 2-chloro-deoxyadenosine, and PCNA ribozyme; (c) migration inhibitors/ECM-modulators such as batimastat, prolyl hydroxylase inhibitors, halofuginone, C proteinase inhibitors, and probucol; and (d) agents that promote healing and re-endotheliazation such as BCP671, VEGF, estradiols (such as 17-beta estradiol (estrogen)), NO donors, EPC antibodies, biorest, ECs, CD-34 antibodies, monocyte chemotactic protein-1, and advanced coatings.

Prosthetic valves comprising an antithrombogenic bioactive agent are particularly preferred for implantation in areas of the body that contact blood. An antithrombogenic bioactive agent is any therapeutic agent that inhibits or prevents thrombus formation within a body vessel. The prosthesis can comprise any suitable antithrombogenic bioactive agent. Types of antithrombotic bioactive agents include anticoagulants, antiplatelets, and fibrinolytics. Anticoagulants are bioactive agents which act on any of the factors, cofactors, activated factors, or activated cofactors in the biochemical cascade and inhibit the synthesis of fibrin. Antiplatelet bioactive agents inhibit the adhesion, activation, and aggregation of platelets, which are key components of thrombi and play an important role in thrombosis. Fibrinolytic bioactive agents enhance the fibrinolytic cascade or otherwise aid is dissolution of a thrombus. Examples of antithrombotics include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic bioactive agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Also particularly preferred are prosthetic valves comprising a thrombolytic therapeutic agent. Thrombolytic agents are used to dissolve blood clots that may adversely affect blood flow in body vessels. A thrombolytic agent is any therapeutic agent that either digests fibrin fibers directly or activates the natural mechanisms for doing so. The prosthesis can comprise any suitable thrombolytic agent. Examples of commercial thrombolytics, with the corresponding active agent in parenthesis, include, but are not limited to, Abbokinase (urokinase), Abbokinase Open-Cath (urokinase), Activase (alteplase, recombinant), Eminase (anitstreplase), Retavase (reteplase, recombinant), and Streptase (streptokinase). Other commonly used names are anisoylated plasminogen-streptokinase activator complex; APSAC; tissue-type plasminogen activator (recombinant); t-PA; rt-PA.

Even more preferable, the therapeutic agent is heparin or hirudin or a derivative thereof. Heparin or Hirudin may be used to prevent inhibited motion or responsiveness of moveable portions of the prosthesis such as valve leaflets or occlusion of the conduit defined by an endovascular prosthesis by limiting platelet deposition on surfaces of endovascular prostheses. Desirably, the frame lumen or groove is loaded with a therapeutic agent. Even more desirably, both the frame lumen and frame apertures are loaded with a therapeutic agent.

Dose Levels of Therapeutic Agents

The therapeutically effective amount of therapeutic agent that is provided in connection with the various embodiments of the present invention ultimately depends upon the condition and severity of the condition to be treated; the type and activity of the specific therapeutic agent employed; the method by which the medical device is administered to the patient; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

Local administration of therapeutic agents may be more effective when carried out over an extended period of time. For example, in one embodiment of the present invention, at least one implantable reservoir may be connected to the frame interior space via a catheter or capillary to continuously supply therapeutic agent to the frame interior space. Reservoirs may be loaded with additional therapeutic agent that may be delivered to the frame interior space as needed. The reservoirs may be reloaded with further therapeutic agent via a syringe and hypodermic needle inserted into the implanted reservoir. Desirably, reservoirs are made of a self-sealing material. A material is self-sealing if it may be punctured, for example by a needle, and, following puncture, seal the site of puncture such that it is not subject to leakage. Even more desirably, reservoirs are made of Thoralon and are implanted in the patient.

The reservoirs may have any suitable configuration. For example, an implanted reservoir may comprise a flat bag or flat cylinder with accordion pleats. Accordion pleats permit the implantable reservoir to have a small collapsed or empty configuration, yet expand substantially about the accordion pleats when filled with therapeutic agent.

Additionally, any number of reservoirs may be implanted with the prosthetic valve. The specific number chosen will depend on several factors, including placement of reservoirs relative to the prosthesis. For example, one reservoir may be implanted posterior to the prosthetic valve (such that when the subject is prone the posterior reservoir is located above the prosthesis) and a second reservoir may be implanted anterior to the prosthesis (such that when the subject is supine the anterior reservoir is located above the prosthesis). A reservoir located above the prosthesis may provide hydrostatic pressure to insure drug flow to the prosthesis frame interior space. One-way check valves may be used with reservoirs to prevent antegrade flow of therapeutic agent back into the reservoir from the frame interior space. For example, when a subject is supine, an anterior reservoir check valve would prohibit therapeutic agent flow into the anterior reservoir from the prosthesis frame interior space or a posterior reservoir. In certain embodiments, where the reservoirs have a positive pressure resulting from stretched reservoir walls, check valves may or may not be necessary.

Delivery of Prosthetic Valves

The prosthetic valves can be configured for delivery to a body vessel. For example, a prosthetic valve can be compressed to a delivery configuration within a retaining sheath that is part of a delivery system, such as a catheter-based system. Upon delivery, the prosthesis can be expanded, for example, by removing a self-expanding frame, or portion thereof, from the sheath or by inflating a balloon from inside the medical device. The delivery configuration can be maintained prior to deployment of the prosthetic valve by any suitable means, including a sheath, a suture, a tube or other restraining material around all or part of the compressed prosthesis, or other methods.

Prosthetic valves can be deployed in a body lumen by any means appropriate to their design. The prostheses of the present invention can be adapted for deployment using conventional methods known in the art and employing percutaneous transluminal catheter devices. The prosthetic valves are designed for deployment by any of a variety of in situ expansion means.

In one embodiment, the prosthetic valve may be mounted onto a catheter that holds the prosthesis as it is delivered through the body lumen and then releases the prosthetic valve and allows it to self-expand into contact with the body lumen. This deployment is effected after the prosthetic valve has been introduced percutaneously, transported transluminally and positioned at a desired location by means of the catheter. The self-expanding prosthetic valve may be deployed according to well-known deployment techniques for self-expanding medical devices. For example, the prosthesis may be positioned at the distal end of a catheter with a removable sheath or sleeve placed over the prosthetic valve to hold the prosthetic valve in a contracted state with a relatively small diameter. The prosthetic valve may then be implanted at the point of treatment by advancing the catheter over a guidewire to the location of the lesion and then withdrawing the sleeve from over the prosthesis. The prosthetic valve will automatically expand and exert pressure on the wall of the blood vessel at the site of the lesion. The catheter, sleeve, and guidewire may then be removed from the patient.

In some embodiments, a bioabsorbable suture or sheath can be used to maintain a self-expanding prosthetic valve in a compressed configuration both prior to and after deployment. As the bioabsorbable sheath or suture is degraded by the body after deployment, the prosthetic valve can expand within the body vessel. In some embodiments, a portion of the prosthesis can be restrained with a bioabsorbable material and another portion allowed to expand immediately upon implantation. For example, a self-expanding frame can be partially restrained by a bioabsorbable material upon deployment and later expand as the bioabsorbable material is absorbed.

In another embodiment, the prosthetic valve is first positioned to surround a portion of an inflatable balloon catheter. The prosthetic valve, with the balloon catheter inside, is configured at a first, collapsed diameter. The prosthesis and the inflatable balloon are percutaneously introduced into a body lumen, following a previously positioned guidewire. For example, in rapid exchange, a rapid exchange prosthesis delivery balloon catheter allows exchange from a balloon angioplasty catheter to a prosthesis delivery catheter without the need to replace the angioplasty catheter guide wire with an exchange-length wire guide before exchanging the catheters. The prosthesis may be tracked by a fluoroscope, until the balloon portion and associated prosthetic valve are positioned within the body passageway at the point where the prosthesis is to be placed. Thereafter, the balloon is inflated and the prosthesis is expanded by the balloon portion from the collapsed diameter to a second expanded diameter. After the prosthetic valve has been expanded to the desired final expanded diameter, the balloon is deflated and the catheter is withdrawn, leaving the prosthetic valve in place. The prosthetic valve may be covered by a removable sheath during delivery to protect both the prosthesis and the vessels.

While the terms "contracted" and "compressed" have been used to describe the prosthesis as having the small diameter necessary for delivery to an implantation site, it will be appreciated that the terms, especially as applied to pressure-expandable prosthetic valves, should not be used to imply that the tube is under external pressure to provide the tube with a small diameter; i.e., a "contracted" or "compressed" pressure-expandable prosthesis may be formed and naturally reside in the "contracted" or "compressed" state until internally pressurized to expand. Therefore, "contracted" and "compressed" are intended only to imply that the prosthetic valve is in a state of having a small diameter relative to an expanded state. It will, therefore, be appreciated by those skilled in the art that yet other modifications could be made to the provided invention without deviating from its spirit and scope as so claimed.

Methods for delivering a prosthetic valve as described herein to any suitable body vessel are also provided, such as a vein, artery, biliary duct, ureteral vessel, body passage or portion of the alimentary canal.

Methods of Treatment and Prevention

Still other embodiments provide methods of treating a subject, which can be animal or human, comprising the step of providing one or more prostheses attached to one or more valve members, as described herein. In some embodiments, methods of treatment may also provide the step of delivering a prosthetic valve to a point of treatment in a body vessel, or deploying a prosthetic valve at the point of treatment, wherein the prosthetic valves are as described herein.

The invention also provides methods of treating a patient. In one embodiment the method comprises a step of delivering a prosthetic valve as described herein to a point of treatment in a body vessel, and deploying the prosthesis at the point of treatment. The delivering step can comprise delivery by surgical or by percutaneous delivery techniques known to those skilled in the art.

Methods for treating and/or preventing certain conditions are also provided, such as venous valve insufficiency, varicose veins, esophageal reflux, restenosis or atherosclerosis. In some embodiments, the invention relates to methods of treating venous valve-related conditions.

While many preferred embodiments discussed herein consider implantation of a medical device in a vein, other embodiments provide for implantation within other body vessels. In another matter of terminology there are many types of body canals, blood vessels, ducts, tubes and other body passages, and the term "vessel" is meant to include all such passages.

The invention includes other embodiments within the scope of the claims, and variations of all embodiments, and is limited only by the claims made by the Applicants.

The invention claimed is:

1. An implantable valve prosthesis comprising:
a frame having compressed and expanded configurations, the frame comprising an exterior wall and a frame segment having an axial length, the exterior wall defining a hollow interior space surrounded by the exterior wall and extending continuously through the frame segment along the axial length, the exterior wall further defining at least one aperture defining a conduit extending through the exterior wall to the hollow interior space;
a valve member operatively connected to the exterior wall and having first and second opposing sides and first and second opposing ends, the first side, second side, and second end being continuously attached to the frame by being wrapped around and surrounding a portion of the frame that includes the frame segment such that the hollow interior space and the at least one aperture are positioned under the wrapped portion of the frame, the first end being free of the frame, the valve member adapted to modify fluid flow through a body lumen; and a therapeutic agent loaded in the hollow interior space in such a way so that at least a portion thereof may pass through the at least one aperture and the valve member.

2. The prosthesis of claim 1, wherein the therapeutic agent is selected from the group consisting of anti-inflammatory/ immunomodulators, antiproliferatives, migration inhibitors/ ECM-modulators, antithrombotics, and thrombolytics.

3. The prosthesis of claim 1, wherein the therapeutic agent is heparin.

4. The prosthesis of claim 1, wherein the therapeutic agent is hirudin.

5. The prosthesis of claim 1, wherein the valve member comprises a biocompatible material which is operatively connected to the exterior wall such that the biocompatible material substantially encapsulates the at least one aperture.

6. The prosthesis of claim 1, wherein the valve member comprises a biocompatible material which is operatively connected to the exterior wall such that the biocompatible material substantially encapsulates the frame.

7. The prosthesis of claim 1, wherein the frame is selected from the group consisting of stainless steel, nitinol, tantalum, a nonmagnetic cobalt-chromium alloy, platinum, titanium, a suitable biocompatible alloy, a suitable biocompatible polymer, a suitable biocompatible material, and a combination thereof.

8. The prosthesis of claim 1, wherein the at least one aperture is between about 0.0001 inches and about 0.010 inches wide.

9. The prosthesis of claim 1, further comprising:
a reservoir for containing therapeutic agent to be delivered to the frame hollow interior; and
a transport device for dispensing therapeutic agent from the reservoir to the hollow interior;
wherein the transport device comprises a proximal end operatively connected with the reservoir and a distal end operatively connected to the hollow interior to facilitate the delivery of the therapeutic agent to the hollow interior through the transport device.

10. The prosthesis of claim 9, wherein the reservoir comprises biocompatible polyurethane.

11. The prosthesis of claim 1, wherein the therapeutic agent is further loaded in the at least one aperture.

12. The prosthesis of claim 1, wherein the valve member comprises a porous polymer.

13. The prosthesis of claim 12, wherein the polymer defines pores that are at least 0.0001 inches wide.

14. The prosthesis of claim 1, wherein the valve member comprises a non-porous polymer.

15. The prosthesis of claim 14, wherein the non-porous polymer has pores cut therein.

16. The prosthesis of claim 15, wherein the pores are at least 0.0001 inches wide.

17. The prosthesis of claim 1, wherein the hollow interior space extends through the entire frame.

18. The prosthesis of claim 17, wherein the entire frame is covered by the valve member.

19. The prosthesis of claim 1, wherein the entire hollow interior space is positioned under the wrapped portion of the frame.

20. The prosthesis of claim 19, wherein the entire frame is covered by the valve member.

* * * * *